United States Patent [19]

Mesek et al.

[11] 3,934,588
[45] Jan. 27, 1976

[54] DISPOSABLE DIAPER HAVING FACING LAYER WITH PATTERNED PREFERENTIAL FLOW AREAS

[75] Inventors: Frederick K. Mesek, Downers Grove; Virginia L. Repke, Oak Forest; William R. Strickel, Chicago, all of Ill.

[73] Assignee: Johnson & Johnson, New Brunswick, N.J.

[22] Filed: Aug. 20, 1974

[21] Appl. No.: 498,891

[52] U.S. Cl............ 128/290 W; 128/287; 128/284
[51] Int. Cl.² ......................................... A61F 13/16
[58] Field of Search........... 128/287, 290 R, 290 W; 161/109, 116

[56] References Cited
UNITED STATES PATENTS

| | | | |
|---|---|---|---|
| 3,240,657 | 3/1966 | Hynek | 161/109 |
| 3,345,243 | 10/1967 | Kalwaites | 161/109 |
| 3,431,911 | 3/1969 | Meisel, Jr. | 128/287 |
| 3,663,348 | 5/1972 | Liloia | 161/116 |
| 3,730,184 | 5/1973 | Mesek | 128/287 |
| 3,814,101 | 6/1974 | Kozak | 128/287 |
| 3,838,694 | 10/1974 | Mesek | 128/290 W |
| 3,848,598 | 11/1974 | Mesek | 128/287 |

*Primary Examiner*—Aldrich F. Medbery

[57] ABSTRACT

A multi-layer diaper includes a porous facing layer to be positioned adjacent an infant's skin, and absorbent batt, and a water-impervious backing sheet. The facing layer is provided with areas of preferential liquid flow, surrounded by areas of increased water repellency relative to the areas of preferential liquid flow. The areas of preferential liquid flow are in the form of thinned areas, areas of increased wettability or areas of normal wettability surrounded by water repellent borders. The flow paths are spread over at least the central portion of the facing layer to direct liquid to the absorbent batt.

22 Claims, 7 Drawing Figures

DISPOSABLE DIAPER HAVING FACING LAYER WITH PATTERNED PREFERENTIAL FLOW AREAS

BACKGROUND OF THE INVENTION

Disposable diapers have met with increased commercial acceptance in recent years, primarily because of their convenience, as opposed to cloth diapers, which must be laundered when soiled. Many different constructions have been proposed, and some have been quite successful in the market place. However, even the more successful diapers are inadequate in certain functional aspects.

One design criterion, which has been sought to be achieved, is the desire to keep moisture away from the surface of the diaper which comes into contact with the infant's skin, and to thereby avoid skin irritation and infection. A diaper that achieves this result to a substantial degree is disclosed in Mesek et al. U.S. Pat. No. 3,612,055, issued Oct. 12, 1971.

The typical disposable diaper is comprised of three components; namely, a facing layer which is positioned adjacent the infant's skin, an absorbent batt immediately beneath the facing layer which distributes and stores the liquid deposited on the diaper, and finally, a water-impervious sheet which contains the liquid within the diaper structure. The facing layer is generally less wettable than the absorbent batt so that liquid will be drawn preferentially into the absorbent batt and away from the infant's skin. To maximize the preferential flow of liquid through the facing layer and into the absorbent batt, it is desirable to reduce the wettability of the facing layer as much as possible. There is, however, a practical limit to the reduction of wettability in the facing layer because when the facing layer becomes sufficiently unwettable, there is some tendency for the liquid deposited on the facing layer to pool on it, and thereby increase the possibility of skin irritation and infection.

SUMMARY OF THE INVENTION

The present invention represents an improvement in disposable diapers in the provision of facing layers therein which function to direct liquid more rapidly to the absorbent batt without undesirable pooling. A facing layer, used in accordance with the present invention, has areas of increased transmissivity for aqueous liquids, referred to as areas of preferential flow, surrounded by borders having less transmissivity for aqueous liquids than the preferantial flow areas.

In prior disposable diapers, the least wettable of the fibrous elements of the diaper is the facing layer so that there is a flow gradient created through the fibrous elements of the diaper. It has been recognized that the facing layer must have the ability to be wetted by water since water repellency can prevent the liquid from penetrating into the facing layer and the absorbent layers behind it, just as a tent fabric holds back penetration of rain water. Contrary to this, it is desirable that the facing layer have some water repellency so that once the liquid has migrated through the facing layer and into the batt, the liquid will be prevented from flowing back through the facing layer and into contact with the infant's skin. The areas of preferential liquid flow of the present invention represents a novel answer to these conflicting criteria, as well as providing a facing layer which prevents pooling of liquid deposited on its outer surface.

In one embodiment of the invention, the preferential flow paths are provided by thinned areas which allow aqueous liquids to flow more rapidly therethrough than through the areas surrounding the thinned areas. The term "thinned areas," as used herein, refers to areas of the facing layer having a lesser amount of the fibers of the facing material and a lesser thickness than adjacent areas. However, these thinned areas always contain some fibers and have some thickness. Thus, the facing layers with thinned areas differ from facing layers made of apertured fabrics since the latter permit dusting of short fibers from the underlying batt unless a layer of tissue paper or similar material is interposed between the batt and the facing layer.

The thinned area facing layer may be comprised of long and short fibers, i.e., textile length and paper making fibers. In one embodiment of the thinned area facing layer, there is a mixture of long and short fibers within the thinned areas and the surrounding areas. In a second embodiment, the thinned areas contain primarily long fibers while the surrounding areas contain a mixture of long and short fibers with a greater proportion of short fibers.

Fibers are usually classified according to length, with relatively long or textile length fibers being longer than about ¼ inch, and generally between ½ and 2 ½ inches in length. The term "long fibers," as used herein, refers to textile fibers having a length greater than ¼ inch, and the fibers may be of natural or synthetic origin. The term "short fibers," as used herein, refers to paper making fibers such as wood pulp fibers or cotton linters, having a length less than about one-quarter inch. The classification of fibers by length may be carried out by the Clark classification procedures described in the test manual of The Technical Association of Pulp and Paper Industry (TAPPI-T233-SU64).

It is recognized that short fibers are substantially less costly than long fibers. It is also recognized in many instances that it is desirable to strengthen the short fiber products by including a blend of long fibers therein.

The facing layers of the present invention are preferably formed by an air-laying process to form a non-woven web material which may be cut to facing layer size. Non-woven materials are structures which, in general, consist of an assemblage or web of fibers, joined randomly or systematically by a mechanical, chemical or other means. These materials are well known in the art, having gained considerable prominence within the last 20 years or so in the consumer market, industrial-commercial market, and the hospital field.

Several methods have been previously disclosed which, with modification, are quite suitable for forming the facing layers of the present invention. In brief summary, these improved air laying techniques for producing non-woven materials involve the individualizing of fibers, dispersing the fibers in high velocity air streams, directing the air streams towards one another, and controlling the amount of mixing, and subsequently condensing the fibers onto a moving foraminous belt to produce a web. Thereafter, the web is generally post treated to provide the required degree of coherence, by one or more well known steps, i.e., mechanical or chemical bonding procedures. These methods are adaptable, as described below, for forming the thinned area preferential flow path facing layers as well as the other facing layer embodiments of the present invention.

Fabrics having thinned areas of preferential liquid flow formed of a mixture of long and short fibers may be made by modification of the method described in the commonly assigned Liloia et al. U.S. Pat. No. 3,663,348, the disclosure of which is hereby incorporated by reference. Specifically, the modified method involves the air deposition of a mixture of individualized long and short fibers on a moving foraminous belt, having blocked areas or onto a high knee screen. In this manner, the fibers moving toward the blocked areas are diverted by the air flow to the unblocked areas, or the fibers deposited on the knee portion of the screen tend to move into the valleys, thereby producing a thinner cross section in the web portions in the blocked areas or on top of the knee.

The thinned area embodiment having a predominance of long fibers in the thinned areas may be formed by the method described in the commonly assigned, copending U.S. application of Goyal et al., Ser. No. 401,918, filed Sept. 28, 1973, the disclosure of which is hereby incorporated by reference. This method involves the production of individual long and short fiber-carrying gaseous streams. The individual streams are directed towards each other so that the fibers in one stream cross over the fibers in the other stream and are deposited on a moving foraminous belt. In this method, the short fibers are directed toward an upstream portion of the belt and tend to migrate into the unblocked areas of the belt or down the sides of the knees and into the valleys therebetween. The long fibers, however, due to their substantial length, and reduced pressure gradient caused by the deposited short fibers, when deposited on the pattern-blocked belt, will lie across the blocked and unblocked areas or when deposited on the high knee screen, will overlay both the knees and valleys. It will be appreciated that this embodiment assures minimum dusting of the short fibers from the facing layer since the outer face will be long fibers which contain the short fibers below their surface.

A second embodiment of the present invention utilizes areas of preferential liquid flow which are formed by adding a wetting agent in selected areas of the facing layer, or more wetting agent in the selected areas than in the other areas of the facing layer. The facing layer of this embodiment is generally uniform in thickness and in composition at any portion of its area, i.e., a uniform mixture of long and short fibers. It may also be uniform in composition at any depth, as described in the above mentioned Liloia et al. patent, or it may vary at different depths in the proportions of long and short fibers as described in the commonly assigned copending Ruffo et al., U.S. application Ser. No. 108,546, the disclosure of which is hereby incorporated by reference.

In this second embodiment, the web is air-laid to a uniform depth onto a belt and treated with a binder to provide structural stability. The binder solution, which will produce water repellency in the facing layer, may contain a small amount of wetting agent so that the entire facing layer will have some wettability. Subsequent to the binder application and preferably after the web has been dried, the fabric is through-printed with a wetting agent in selected areas to provide areas of preferential liquid flow through the facing layer.

A third embodiment of this invention utilizes preferential flow paths which are formed by providing boundary areas around the preferential liquid flow area which have less wettability. The fabric used for the facing layer of this embodiment may be initially formed without using a binder solution so that the fabric has little water repellency or may be formed with a binder that has a large amount of wetting agent to counteract the water repellency of the binder. After the fabric has been dried, it is through-printed with a water-repellent binder in the area surrounding the areas which are to form the areas of preferential liquid flow.

The fabric of the second and third embodiments described above are similar in that each fabric there is greater wettability in the areas of preferential liquid flow than in the surrounding areas. They differ, however, in that the second embodiment provides a maximum total add-on (of binder and wetting agent) in the areas of preferential flow while the third embodiment provides a maximum total add-on in the surrounding areas.

While the above-mentioned facing layers are fibrous in nature, the present invention may also be embodied in other types of facing layers, such as those disclosed in Meisel, U.S. Pat. No. 3,431,911. The Meisel patent discloses a facing layer formed by an open-celled polymeric foam material, such as polyether or polyester-polyurethane foams. By forming this type of polymeric material with thinned areas, or selectively posttreating portions of it with wetting and/or water-repellent agents, areas of preferential liquid flow may be produced.

The pattern of preferential liquid flow areas within the facing layer of the improved diaper may take on a variety of shapes, including circular, rectangular, diamond-shaped, etc. The shapes of the preferential liquid flow areas should have a minimum dimension of at least one-quarter inch, and should produce a ratio of preferential liquid flow area to total facing flow area to total facing surface area in the range of 4% to 40%. They should also be spaced no farther apart than two inches from each other so that no point on the facing layer in the central area of initial wetting is more than about one inch from at least one preferential liquid flow area. The preferential liquid flow areas may be spread over the entire area of the facing layer, or may, if desired, be spread over a central area, leaving the marginal areas (where initial wetting is unlikely) as a water-repellent border having a width of about one to two inches.

With such a distribution, in any embodiment utilizing these preferential liquid flow areas, liquid deposited on one surface of the facing layer will be quickly drawn into the diaper to the absorbent batt below the facing layer. The areas bordering the preferential flow paths provide resistance to transverse movement of fluid within the facing layer, thus minimizing the wetted area and the tendency for skin irritation or infection. Moreover, once the liquid has been drawn into the absorbent batt and has spread laterally therein, fluid pressure within the batt is decreased so that the tendency to return through the preferential liquid flow areas is reduced, and the areas bordering the preferential liquid flow areas provide a barrier to the return of fluid through the facing layer.

DETAILED DESCRIPTION

Figure 1:
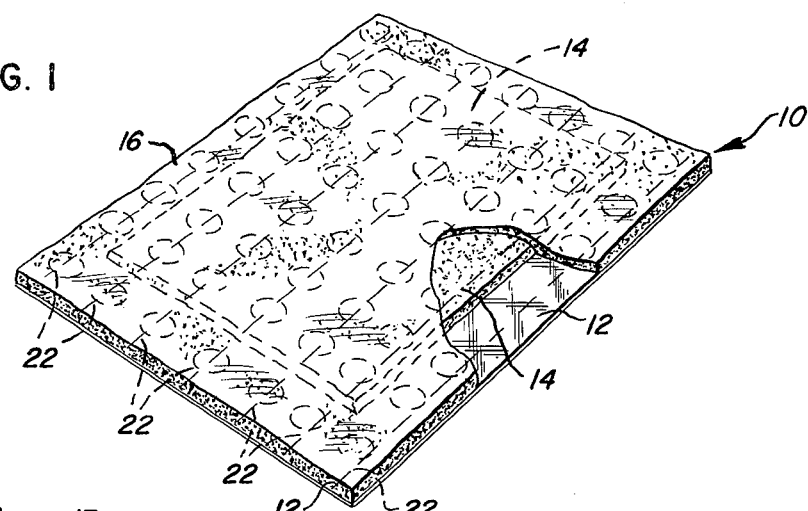
FIG. 1 is a perspective view, with certain portions broken away, of an open unfolded diaper including a facing layer in accordance with the present invention.

While this invention is susceptible of embodiment in many different forms, there is shown in the drawings and will herein be described in detail, only preferred embodiments of the invention with the understanding that the present disclosure is to be considered as an exemplification of the principles of the invention, and is not intended to limit the invention to the embodiments illustrated.

Referring to the drawings, and particularly to FIG. 1, the diaper assembly 10, when fully opened and laid out flat, comprises a lowermost water-impervious sheet 12, which is rectangular in shape, a highly absorbent pad, or batt 14, which is also rectangular in shape, but smaller than the impervious sheet and centrally disposed thereon, and an over-laying facing layer 16 of fibrous material, which is also rectangular in shape, equal in dimension, and coterminous with the impervious sheet, and in contact therewith in the marginal portions of the diaper extending peripherally beyond the absorbent batt.

The batt 14 may have a continuous paper-like densified highly compacted lowermost fibrous layer integral therewith that includes spaced, parallel and longitudinally disposed thickened densified portions. The thickened densified portions are formed by further compression of the batt 14 while it is still moist, as described in Repke U.S. Pat. application Ser. No. 376,193, filed July 21, 1973, as with embossing rollers which produce recesses in the surface of the batt 14 in line with the thickened portions.

The lower major surface of the batt, including the densified layer, is adhered to the impervious sheet by bead lines 22 of adhesive substantially throughout the area of the interface therebetween. Marginal portions of the facing layer 16, extending beyond the batt 14, are also adhered to the impervious sheet by adhesive bead lines 22.

In the preferred embodiment of the invention, a moisture-impervious sheet 12 is formed of polyethylene having a thickness of approximately 0.001 inch. The sheet may be smooth or it may be embossed to improve its drape and feel. Other suitable flexible moisture impervious sheets may be used in accordance with the invention, such as, for example, polyethylene terephthalate sheets having a thickness of about 0.0005 inch.

Batt 1r may be formed of loosely compacted short cellulosic fibers, such as wood pulp fibers, or cotton linters, or mixtures thereof, which are primarily held together by interfiber bonds requiring no adhesive, as is known in the art. Briefly, this batt is a low bulk density coherent web of loosely compacted cellulosic fibers preferably comminuted wood pulp fibers in the form of so-called "fluff."

The paper-like densified layer of batt 14 is formed by a slight moistening of one surface of the batt followed by the application of pressure thereto. The nature of the batt and its densified layer and method of producing the same are described, generally, in U.S. Pat. No. 3,017,304.

The composite density of batt 14, including its densified layer, should be above about 0.07 grams/cc. and preferably between about 0.10 and 0.15 grams/cc. The foregoing density values are applicable to the diaper as produced. In storage and handling the loft or thickness of the batt is increased to some extent, resulting in lower densities.

The facing layer may be made up of fibers consisting predominately of low cost short fibers, such as wood pulp fibers or cotton linters in amounts of about 75 to about 98%, the balance being long fibers such as rayon. Short fibers, such as wood pulp fibers or cotton linters, are substantially less expensive than textile length fibers such as cotton and rayon, and this low cost is a factor in reducing the cost of the facing layer component of the diaper of this invention. In the facing layer 16, the long fibers may be 1.5 denier rayon fibers uniformly cut to 1½ inch length. The short and long fibers are randomly dispersed and bonded with a bonding agent such as crosslinking acrylic emulsion. The facing layer is also treated with a wetting agent, such as a non-ionic surfactant, to partially counteract the water-repellency of the bonding agent and bring the facing layer to the desired degree of wettability.

An important aspect of this invention is the provision for selective wettability among the above-mentioned fibrous components of the diaper, such that the moisture is selectively draw from the facing layer into the body of the batt and then from the body of the batt into the densified layer thereof. In the present invention, the facing layer 16 is provided with areas of preferential liquid flow to direct the liquid quickly to the absorbent batt 14. The term "areas of preferential liquid flow," as used herein, refers to areas in the facing layer having a higher degree of water transmissivity than the areas surrounding them. The preferential flow paths extend through the thickness of the facing layer and are surrounded by borders having less water transmissivity than that of the preferential flow paths. With respect to liquid flow, the preferential flow paths may be considered comparable in behavior to "holes" in the facing layer. However, a perforated fabric would not be suitable as the facing fabric of this invention because its apertures permit dust passage, as well as liquid passage, and would therefore permit undesirable "dusting" of the short fibers of the absorbent batt.

The preferential flow paths of the present invention are positioned in spaced areas of the facing layer, preferably uniformly spaced in a repetitive pattern across the facing layers. The individual preferential liquid flow areas may be of a variety of geometric shapes including, but not limited to circular, rectangular and diamond shapes, subject to a minimum dimension of ¼ inch. The repetitive pattern may be continuous across the surface of the facing layer or may be positioned in a selected area which overlays the absorbent batt or the central portion thereof. The ratio of the total area of the preferential liquid flow areas to the surface area of the facing layer or to the central portion thereof which contains the preferential liquid flow areas is preferably in the range of 4 to 40%. The preferential liquid flow areas are arranged such that any liquid deposited on the facing layer, or on the central portion thereof, is not more than one inch from at least one of these areas. Thus, any liquid will be quickly drawn into the preferential liquid flow areas contiguous to the deposition site and into the absorbent batt where it will be spread laterally.

Figure 2:
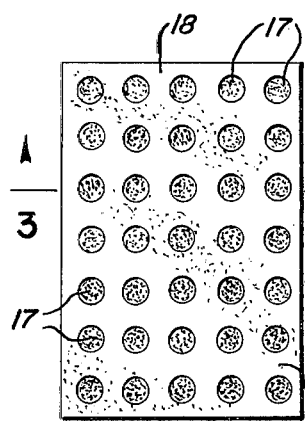
FIG. 2 is a top plan view on a reduced scale of the facing layer of FIG. 1.
Figure 3:
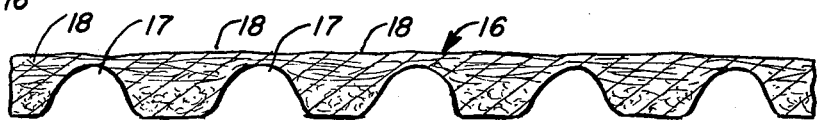
FIG. 3 is an enlarged sectional view of the facing layer of FIG. 2, taken along plane 3—3, illustrating the internal structure.

The facing layer illustrated in FIGS. 1 to 3 has areas 17 of preferential liquid flow which are formed by thinned areas in the facing layer 16. The preferred thinned area fabric may have either of two types of thinned areas, one having a substantially uniform blend of long and short fibers and one in which the thinned areas have predominately long fibers.

In the substantially uniformly blended thinned area facing layer, the density of fibers is substantially uniform through the facing layer 16. In the illustrated embodiment, the thinned areas 17 are circular in cross section as viewed from the top of the facing layer (FIG. 2). The undersurface of the facing layer is concave in the areas of reduced thickness with gradually increasing thickness from the center of each preferential flow path to the bordering areas 18 surrounding the paths. Since the entire facing layer 16 has the same wettability, liquid deposited in the top surface of the facing layer will pass more quickly through the thinned areas 17 which provide less resistance to flow than the bordering areas 18. The liquid will tend to flow preferentially into the absorbent batt 14 beneath the facing layer rather than into the bordering areas 18 surrounding the preferential flow paths, since, as noted above, the batt 14 has greater wettability than the facing layer. After the liquid has been drawn into the batt 14, wherein it is spread laterally, the areas 18, surrounding the areas of preferential liquid flow, act as barriers against the return flow of liquid to the top of the facing layer 16. The thinned areas 17 not only allow liquid to flow quickly therethrough, but by virtue of the presence of fibers therein, dusting of short fibers from the inner face of the facing layer 16 and the absorbent batt 14 is prevented.

Thinned areas in a fabric having a uniform fiber distribution throughout its thickness may be formed by modifying the above mentioned Liloia et al. method to include a patterned blocked foraminous belt or knee screen.

In a second thinned area embodiment, the areas of preferential liquid flow 17 are characterized by a predominance of long fibers. This type of thinned area is produced by the above-mentioned Goyal et al. method by depositing short fibers upstream on a high knee screen or on a foraminous belt with blocked areas and depositing long fibers at a downstream location over the short fibers. During this process, the short fibers tend to follow the flow lines of the gaseous streams and move into the valleys between the high points in the knee screen or to the unblocked areas of the belt. The long fibers, however, extend beyond the flow lines of the gaseous streams in which they are entrained, and therefore, will remain on the high portions of the knee screen as well as in the valley portions thereof or will stretch across the blocked and unblocked areas. It will be appreciated that in this type of thinned area in which the lower portion of the facing layer is predominately short fibers that the long fibers on the outer surface will also prevent dusting of the short fibers from the facing layer 16 and the absorbent batt 14.

Figure 4:
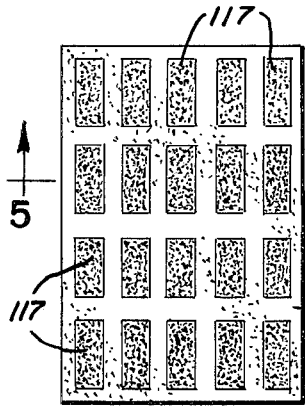
FIG. 4 is a top plan view of a second embodiment of the facing layer.
Figure 5:
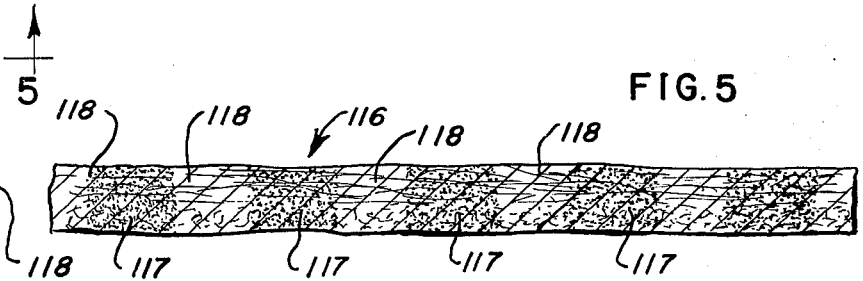
FIG. 5 is an enlarged sectional view of the facing layer of FIG. 4, taken along plane 5—5, illustrating the internal structure.

Referring now to FIGS. 4 and 5, a second type of facing layer having areas of preferential liquid flow, is denoted in its entirety by numeral 116. Facing layer 116 is structurally uniform having a uniform composition in all portions of its area and depth, and in the preferred embodiment is a uniform mixture of long and short fibers. Facing layer 116 may be produced by an air-laying process, such as described in the above-mentioned Liloia et at. patent. The areas of preferential liquid flow 117 are provided in this embodiment by the addition of a greater amount of wetting agent in the selected areas than by the other areas of the facing layer. After the web from which the facing layer 116 will be cut has been formed, the web is treated with a bonding agent, such as a self-cross linking acrylic emulsion. One bonding agent which has been employed with considerable success is a latex of a polyethylacrylate copolymer containing small amounts of acrylonitrile and a cross-linkage monomer sold under the trademark HYCAR 2600 × 120. A small amount of wetting agent may also be added to the bonding agent to partially counteract the water repellency of the binder. Typical wetting agents or surfactants which have been found to be suitable, are the non-ionic polyoxyethylene sorbitan monolaurate sold under the trademark TWEEN 20, and the ionic sulfonated alkyl ester sold under the trademark TRITON GR-5. After the fabric has been treated with the binder solution (and wetting agent, if any) and dried, the fabric is through-printed by known techniques with additional wetting agent to produce the areas 117 of preferential liquid flow.

As illustrated in FIG. 5, the areas 117 of preferential liquid flow extend completely through the crosssectional thickness of the facing layer 116 to provide an uninterrupted flow path for liquid from the top of the facing layer to the absorbent batt 14 immediately below the facing layer.

Figure 6:
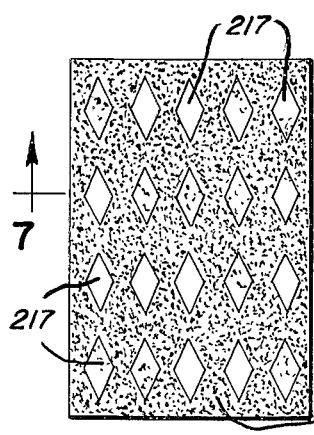
FIG. 6 is a top plan view of a third embodiment of the facing layer.
Figure 7:
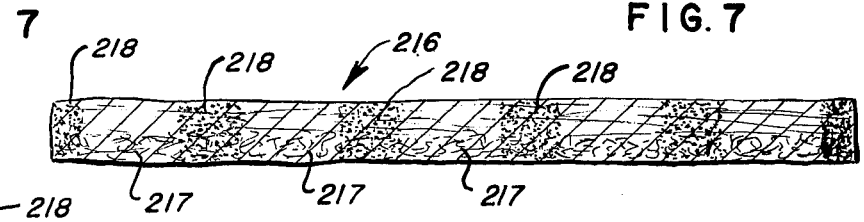
FIG. 7 is an enlarged sectional view of the facing layer of FIG. 6, taken along plane 7—7, illustrating the internal structure.

The facing layer 216 illustrated in FIGS. 6 and 7 is related to the facing layer 116, except that differential wettability is achieved in layer 216 by different levels of binder application, rather than different levels of surfactant application. Facing layer 216 may be of the nonwoven air-laid fibrous type. After the fabric from which the facing layer 216 will be cut has been laid, two different methods may be employed to form the preferential liquid flow areas 217. It will be appreciated that a uniform fabric of long and short fibers has a high degree of wettability if no binder solution is applied to the fabric. Accordingly, the areas of preferential liquid flow 217 may be formed by throughprinting the bordering areas 218, surrounding the preferential liquid flow areas with a binder solution, such as the abovementioned binder solution. In this manner, the borders 218 have substantially less wettability than the untreated areas and therefore define the areas 217 of preferential liquid flow.

In some circumstances it may be desirable to have the fibers in areas 217 bonded more strongly to each other and to the bordering areas 218. Accordingly, the fabric from which the facing layer 216 will be cut may be treated initially with a mixture solution of binder and wetting agent so that the fabric has structural stability and wettability uniformly throughout its cross section. This uniformly treated fabric is then through-printed with additional binder solution in the bordering areas to decrease the wettability of the border areas relative to the preferential liquid flow path areas 217.

The preferred size and spacing of the preferential liquid flow areas in the embodiments of FIGS. 4 and 5 and FIGS. 6 and 7 are similar to those discussed above in relation to the thinned area embodiment of FIG. 3.

The present invention may also be embodied in a variety of other facing layers such as an open-cell, polymeric foam material which may be formed with a surface having declivities spaced from each other and in the desired shape to produce thinned areas within the foam material, or a uniform layer of polymeric foam may be selectively treated to produce areas of increased hydrophobicity or bordering areas of decreased hydrophobicity in accordance with the present invention.

The invention may also be embodied in a facing layer made with only short fibers but containing sufficient binder to provide the necessary strength and integrity. Here again, preferential liquid flow areas can be provided by thinned areas or by areas of increased wettability, obtained as described above.

It is also to be noted that the nature of the batt may also be changed without departing from the scope of this invention, provided that the batt is more wettable than the facing layer. Batts made of a plurality of plies of cellulose wadding may be used, for example, if desired.

Other modifications and variations will be apparent to those skilled in the art.

What is claimed is:

1. A multi-layer diaper comprising: a porous, imperforate facing layer in the form of a non-woven fabric formed of long fibers and short fibers, said facing layer having separate and discrete areas of preferential liquid flow throughout at least the central portion of its areas arranged sufficiently closely to each other so that no point in the central portion of the facing layer is more than one inch away from an area of preferential liquid flow; a highly porous, loosely compacted, cellulosic fibrous batt in face-to-face juxtaposition with the inner face of said facing layer; and a water-impervious backing sheet adhered to the outer surface of said batt.

2. The diaper of claim 1 wherein said areas of preferential liquid flow are formed by thinned areas, having fewer fibers than the other areas of said facing layer.

3. The diaper of claim 2 wherein the fibers in said thinned areas are characterized by a substantially uniform mixture of long and short fibers.

4. The diaper of claim 2 wherein the fibers in said thinned areas are primarily long fibers.

5. The diaper of claim 2 wherein said thinned areas are concave on one face of said facing layer, said batt being in juxtaposition with said face.

6. The diaper of claim 1 wherein said areas of preferential liquid flow are formed by areas having higher wettability than the other areas of said facing layer.

7. A multi-layer diaper comprising: a porous facing layer having separate and discrete areas of preferential liquid flow across at least the central portion of its area arranged sufficiently closely to each other so that urine discharged at any point on at least the central portion of the facing layer is rapidly transported through said facing layer without forming a pool thereon said facing layer being imperforate and all portions of said facing layer being previous to liquid flow therethrough; a highly absorbent batt in face-to-face juxtaposition with the inner face of said facing layer; and a water-impervious backing sheet adhered to the other surface of said batt.

8. The diaper of claim 7 wherein said highly absorbent batt comprises a highly porous, loosely compacted, cellulosic fibrous batt.

9. The diaper of claim 7 wherein said highly absorbent batt comprises a plurality of plies of cellulose wadding.

10. The diaper of claim 7 wherein said discrete areas of preferential liquid flow are spaced so that no point on at least the central area of said facing layer is more than one inch away from at least one area of preferential liquid flow.

11. The diaper of claim 10 wherein said areas of preferential liquid flow are formed by thinned areas having less material thickness than the surrounding areas of said facing layer.

12. The diaper of claim 10 wherein said facing layer comprises a non-woven fibrous layer.

13. The diaper of claim 10 wherein said facing layer comprises a flexible, open-celled polymeric foam material.

14. The diaper of claim 10 wherein said facing layer is of uniform thickness and said areas of preferential liquid flow are formed by areas having higher wettability than the other areas of said facing layer.

15. The diaper of claim 14 wherein said facing layers contains a wetting agent in said areas of preferential liquid flow.

16. The diaper of claim 15 wherein the area surrounding said areas of preferential liquid flow contain a wetting agent, but less wetting agent than said areas of preferential liquid flow.

17. The diaper of claim 14 wherein said facing layer contains a water repellent bonding agent distributed in a pattern surrounding said areas of preferential liquid flow.

18. The diaper of claim 14 wherein said facing layer contains a uniform distribution of a water repellent bonding agent and contains a wetting agent in selected areas to counteract said water repellent bonding agent, thereby forming said areas of preferential liquid flow.

19. The diaper of claim 10 wherein said preferential liquid flow areas are at least ¼ inch at their minimum dimension.

20. The diaper of claim 10 wherein said preferential liquid flow areas are arranged in a pattern throughout the entire area of said facing layer.

21. The diaper of claim 10 wherein said batt is smaller than said facing layer and said preferential liquid flow areas are arranged in a pattern in the area of said facing layer over-laying the absorbent batt.

22. The diaper of claim 10 wherein the ratio of the total of preferential flow areas to the facing layer area is in the range of 4 to 40%.

* * * * *